(12) United States Patent
Ohashi et al.

(10) Patent No.: US 6,616,709 B2
(45) Date of Patent: Sep. 9, 2003

(54) HAIR DYE COMPOSITION

(75) Inventors: Yukihiro Ohashi, Sumida-ku (JP); Hajime Miyabe, Sumida-ku (JP); Kenichi Matsunaga, Sumida-ku (JP); Shintaro Totoki, Sumida-ku (JP); Yoshinori Saito, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/887,473

(22) Filed: Jun. 25, 2001

(65) Prior Publication Data

US 2002/0088063 A1 Jul. 11, 2002

(30) Foreign Application Priority Data

Jun. 27, 2000 (JP) ........................................ 2000-193175

(51) Int. Cl.$^7$ ................................................ A61K 7/13
(52) U.S. Cl. ........................ 8/405; 8/406; 8/407; 8/409; 8/410; 8/454; 8/455; 546/167
(58) Field of Search ........................... 8/405, 406, 407, 8/409, 410; 546/167

(56) References Cited

U.S. PATENT DOCUMENTS

| | | | |
|---|---|---|---|
| 3,933,847 A | 1/1976 | Ohkawa et al. | 260/309.2 |
| 4,138,570 A | 2/1979 | Psaar | 548/379 |
| 4,201,707 A | 5/1980 | Psaar | 260/162 |
| 4,220,780 A | * 9/1980 | Brack | 546/167 |
| 4,276,415 A | 6/1981 | Degen et al. | 542/435 |
| 5,733,343 A | 3/1998 | Möckli | 8/426 |
| 5,879,412 A | * 3/1999 | Rondeau et al. | 8/411 |
| 5,888,252 A | 3/1999 | Möckli | 8/426 |
| 5,980,587 A | 11/1999 | Samain | 8/426 |

FOREIGN PATENT DOCUMENTS

| | | |
|---|---|---|
| JP | 49-87730 | 8/1974 |
| JP | 51-136723 | 11/1976 |
| JP | 53-139634 | 12/1978 |
| JP | 55-99955 | 7/1980 |
| JP | 6-271435 | 9/1994 |
| JP | 8-501322 | 2/1996 |
| JP | 8-507545 | 8/1996 |
| JP | 10-502946 | 3/1998 |
| JP | 10-194942 | 7/1998 |

OTHER PUBLICATIONS

K. Schaefer, et al., DWI Reports, No. 109, pp. 699–716, XP–001145854, "Fluoreszenzmikrokopische Untersuchung Der Diffusion Von Farbstoffen In Keratinfasern", 1992.
Database Registry 'Online !, Chemical Abstracts, pp. 1–2, XP–002235278, "1H–Benzimidazolium, 2–'7–(Diethylamino)–2–Oxo–2H–1–Benzopyran–3–yl !–1, 3–Dimethyl–, Trichlorozincate", 2000.

* cited by examiner

Primary Examiner—Mark Kopec
Assistant Examiner—Eisa Elhilo
(74) Attorney, Agent, or Firm—Oblon, Spivak, McClelland, Maier & Neustadt, P.C.

(57) ABSTRACT

Provided is a hair dye composition containing a direct dye (1). This hair dye composition has markedly high hair dyeing power, has less color fade over time and undergoes a small change in the color tone of the dye after storage.

(1)

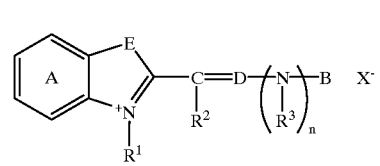

wherein, ring A may represents a benzene ring which may have a substituent or the like, B represents an aryl or heterocyclic group, D represents N or $CR^4$ (wherein $R^4$ represents H or alkyl), E represents $NR^5$, $CR^6R^7$ or $CR^6=CR^7$ (wherein $R^5$ represents alkyl or the like, and $R^6$ and $R^7$ each represents H or alkyl) or, O or S, $R^1$ represents alkyl or the like, and n stands for 0 or 1, with the proviso that at n=0, $R^2$ and $R^5$ form, when taken together with N—C—C, a heterocycle, or $R^2$ is bonded to B, thereby forming a heterocycle and at n=1, $R^2$ and $R^3$ form, when taken together with C=D—N, a heterocycle, and $X^-$ represents an anion.

17 Claims, No Drawings

HAIR DYE COMPOSITION

TECHNICAL FIELD

The present invention relates to a hair dye composition having markedly high dyeing power, can strongly impart the hair with an extremely vivid color ranging from greenish yellow, yellow, red to blue, has less color fade over time and undergoes a small change in the color tone of the dye even after storage.

BACKGROUND ART

Hair dyes can be classified by the dye to be used therefor, or whether they have bleaching action of melanin or not. Typical examples include a two-part permanent hair dye composed of a first part containing an alkali agent, an oxidation dye and a direct dye such as nitro dye and a second part containing an oxidizing agent; and one-part semi-permanent hair dye containing an organic acid or an alkali agent, and a direct dye such as acid dye, basic dye or nitro dye.

The above-described permanent hair dye is however accompanied with the drawbacks that color tone imparted by an oxidation dye is not so vivid and the color of the hair dyed with a vivid-color producing nitro dye ordinarily employed as a direct dye markedly fades over time and becomes dull soon even if the color tone rightly after dyeing is very vivid (Japanese Patent Application Laid-Open (Kokai) No. Hei 6-271435).

Recently, hair dyes containing as a direct dye a so-called cationic dye having a cation group contained in their conjugate system have been reported (Japanese Language Laid-Open Publication (PCT) No. Hei 8-507545, 8-501322 or 10-502946, or Japanese Patent Application Laid-Open (Kokai) No. Hei 10-194942). They have been found to involve drawbacks that intended dyeing effects are not available owing to decomposition of them caused by mixing, upon hair dyeing, with hydrogen peroxide ordinarily employed as an oxidizing agent; and that when a cationic group is contained in an azo-based (—N=N—) conjugated system, they are unstable to an alkali agent or a reducing agent essentially contained in a permanent hair dye.

DISCLOSURE OF THE INVENTION

An object of the present invention is to provide a hair dye composition having high hair dyeing power, less color fade over time, and excellent storage stability to permit only a smaller change in color tone of the dye after storage.

The present inventors have found that use of the below-described compound—which is known in Japanese Patent Applications Laid-Open (Kokai) Nos. Sho 49-87730, 53-139634, 51-136723 and 55-99955 as a cationic dye for dyeing or printing therewith synthetic resins, synthetic fibers, paper or leather—as a hair dye, the resulting hair dye composition can strongly impart the hair with an extremely vivid color ranging from greenish yellow, yellow, red to blue without decomposing the dye upon hair dyeing, exhibits excellent light resistance, washing resistance, perspiration resistance, friction resistance and heat resistance, and undergoes a small change in the color tone of the dye after storage as compared with that rightly after preparation because the dye exists in the composition stably.

In one aspect of the present invention, there is thus provided a hair dye composition comprising, as a direct dye, a compound represented by the following formula (1):

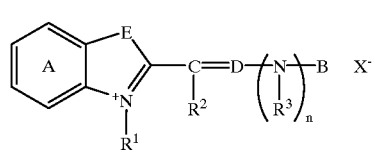

(1)

wherein, ring A represents a benzene ring which may have a substituent or may further be cyclocondensed with another aromatic ring;

B represents an aryl group which may have a substituent or may be coupled with $R^2$ to form a heterocyclic structure which will be described later, or a heterocyclic group which may have a substituent or may be coupled with $R^2$ to form a heterocyclic structure which will be described later, D represents a nitrogen atom or a group $CR^4$ (in which $R^4$ represents a hydrogen atom or a $C_{1-6}$ alkyl group);

E represents a group $NR^5$, $CR^6R^7$ or $CR^6=CR^7$ (in which $R^5$ represents a $C_{1-6}$ alkyl group which may have a substituent, a $C_{2-6}$ alkenyl group which may have a substituent or an aryl group which may have a substituent, or forms, when taken together with $R^2$, a ring which will be described later, and $R^6$ and $R^7$ each independently represents a hydrogen atom or a $C_{1-6}$ alkyl group), an oxygen atom or a sulfur atom;

$R^1$ represents a $C_{1-6}$ alkyl group which may have a substituent, a $C_{2-6}$ alkenyl group which may have a substituent or an aryl group which may have a substituent;

$R^2$ represents a divalent group bonded to B or forms, when taken together with $R^3$ or $R^5$, a ring which will be described later, $R^3$ forms, when taken together with $R^2$, a ring which will be described later;

n stands for 0 or 1, with the proviso that when n=0, $R^2$ and $R^5$, when taken together with N—C—C, form a 5- to 7-membered nitrogen-containing heterocyclic structure which may have a substituent, or $R^2$ is bonded to B, thereby forming a 6- or 7-membered heterocyclic structure which may have a substituent and may contain a hetero atom other than D and when n=1, $R^2$ and $R^3$, when taken together with C=D—N, form a 5- to 7-membered nitrogen-containing heterocyclic structure which may have a substituent, and $X^-$ represents an anion.

In another aspect of the present invention, there is also provided a method for dyeing the hair with the above-described hair dye composition.

BEST MODE FOR CARRYING OUT THE INVENTION

In the formula (1), examples of the substituent which the ring A may have include alkyl groups, aryl groups, alkoxy groups, amino group, hydroxy group, cyano group, nitro group and halogen atoms, more specifically, methyl group, ethyl group, methoxy group, ethoxy group, chlorine atom and bromine atom. Examples of the aromatic ring with which the ring A may be cyclocondensed include a benzene ring.

Examples of the aryl group represented by B include phenyl, 1-naphthyl and 2-naphthyl groups, while those of the heterocyclic group include 2-benzthiazolyl and 3-indolyl groups, each of which may be substituted with a chlorine atom, bromine atom, nitro group, cyano group, $C_{1-4}$ alkyl group, phenyl group, benzyl group, $C_{1-4}$ alkoxy group, hydroxy group, phenoxy group, benzyloxy group, $C_{1-4}$ alkylsulfonyl group, phenylsulfonyl group, benzylsulfonyl group, aminocarbonyl group, mono- or di-($C_{1-4}$ alkyl) aminocarbonyl group, aminosulfonyl group, $C_{1-4}$ alkylcarbonyl group, $C_{1-4}$ alkylcarbonylamino group, benzoylamino group, phenylazo group, and a group $NR^8R^9$ (in which $R^8$ and $R^9$ each independently represents a hydrogen atom, $C_{1-4}$ alkyl group, aryl group, aralkyl group, unsubstituted or mono- or di-($C_{1-4}$ alkyl)-substituted amino($C_{1-4}$ alkyl) group, amino($C_{1-4}$ alkyl) group substituted by a group of the formula (1) from which one hydrogen atom has been removed, or ($C_{1-4}$ alkoxy) ($C_{1-4}$ alkyl)amino group). The number of these substituents is 1 to 3. The cycle-constituting atom may be coupled with the above-exemplified substituent to form another cyclic structure.

Examples of the $C_{1-6}$ alkyl group represented by $R^4$ in the case where D represents a group $CR^4$ or by $R^6$ or $R^7$ in the case where E represents a group $CR^6R^7$ or $CR^6=CR^7$ include methyl, ethyl, propyl, isopropyl and cyclohexyl groups. Preferred examples of $R^4$, $R^6$ or $R^7$ include hydrogen atom and methyl groups.

Examples of the $C_{1-6}$ alkyl group represented by $R^5$ in the case where E represents a group $NR^5$ include methyl, ethyl, propyl, isopropyl and cyclohexyl groups; those of the $C_{2-6}$ alkenyl group include ethenyl and propenyl groups; and those of the aryl include phenyl and naphthyl groups, each of which may be substituted with an aryl, alkoxy, amino, hydroxy or cyano group, or a halogen atom.

Examples of the $C_{1-6}$ alkyl group represented by $R^1$ include methyl, ethyl, propyl, isopropyl and cyclohexyl groups, those of the $C_{2-6}$ alkenyl group include ethenyl and propenyl groups, and those of the aryl group include phenyl and naphthyl groups, of which the alkyl group is preferred as $R^1$. Examples of the group which may be a substituent for them include aryl groups, cyano group, halogen atoms, hydroxy group, $C_{1-4}$ alkoxy groups, $NR^{10}R^{11}$ (in which $R^{10}$ and $R^{11}$ each independently represents a hydrogen atom, $C_{1-4}$ alkyl group, aryl group, aralkyl group, unsubstituted or mono- or di($C_{1-4}$ alkyl)substituted amino($C_{1-4}$ alkyl) group, or ($C_{1-4}$ alkoxy) ($C_{1-4}$ alkyl)amino group) and a group of the formula (1) from which one hydrogen atom has been removed.

Examples of the $R^5$–$R^2$ or $R^2$–$R^3$ in the case where a 5- to 7-membered nitrogen-containing heterocyclic structure which may have a substituent is formed by $R^2$ and $R^5$ when they are taken together with N—C—C at n=0, or by $R^2$ and $R^3$ when taken together with C=D—N at n=1, include groups represented by —$(CR^{12}R^{13})_m$— (in which $R^{12}$ and $R^{13}$ each independently represents a $C_{1-4}$ alkyl group and m stands for an integer of 2 to 4).

Examples of the divalent group, as $R^2$, bonded to B in the case where a 6- or 7-membered heterocyclic structure which may have a substituent and may have a hetero atom other than D is formed by bonding of $R^2$ to B when n=0 include groups —CH=N— and —CO—O—.

Examples of the anion represented by $X^-$ include chloride ions, bromide ions, iodide ions, trichlorozincic acid ions, tetrachlorozincic acid ions, sulfuric acid ions, hydrosulfuric acid ions, methyl sulfate ions, phosphoric acid ions, formic acid ions and acetic acid ions.

Specific examples of the direct dye (1) to be used in the present invention will next be shown.

Compound (a)

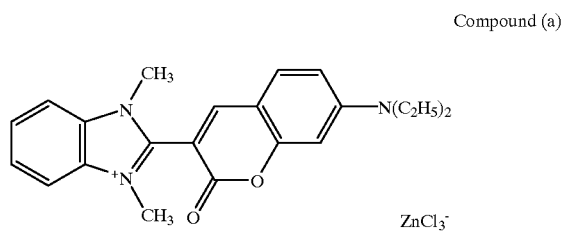

Compound (b)

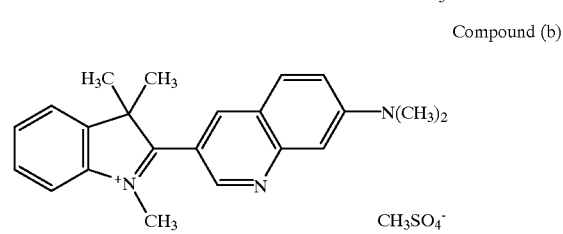

Compound (c)

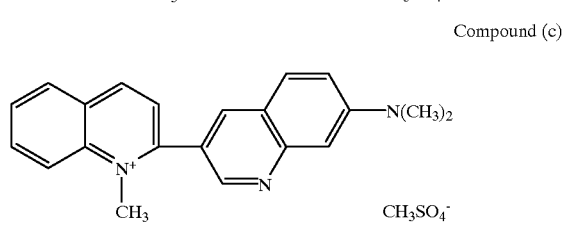

Compound (d)

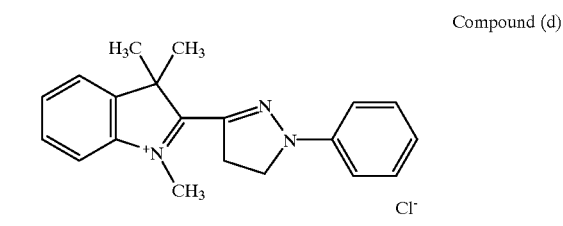

Compound (e)

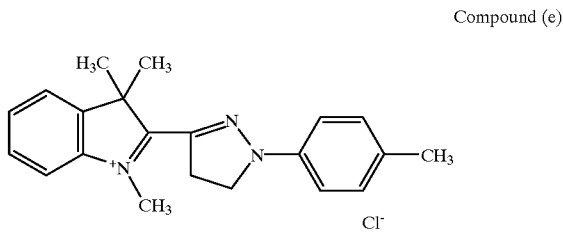

Compound (f)

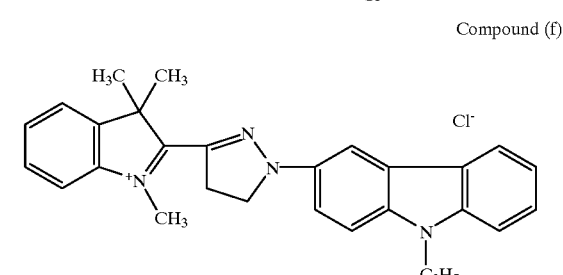

Compound (g)

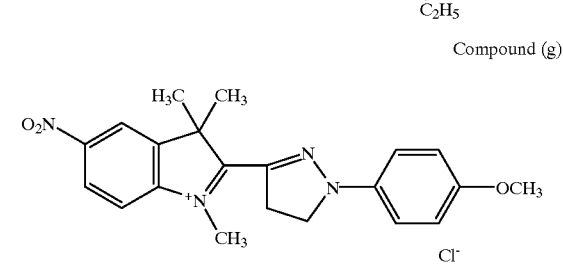

-continued

Compound (h)
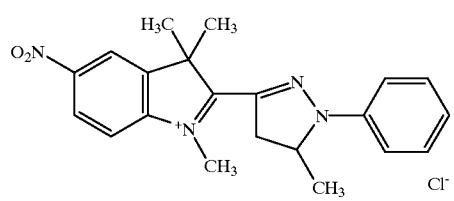

Compound (i)
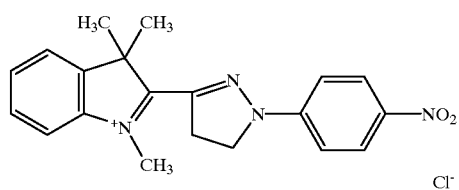

Compound (j)
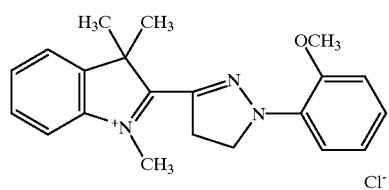

Compound (k)
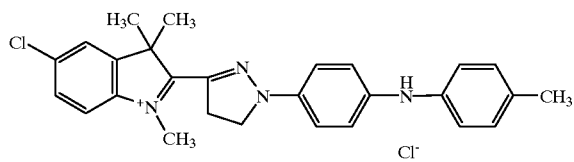

Compound (l)
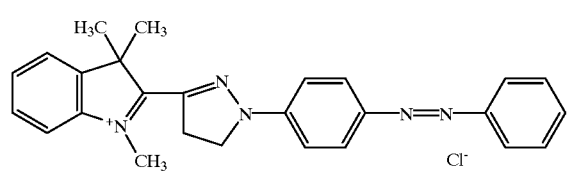

Compound (m)
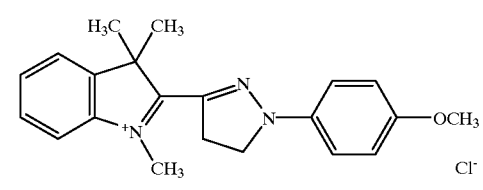

Compound (n)
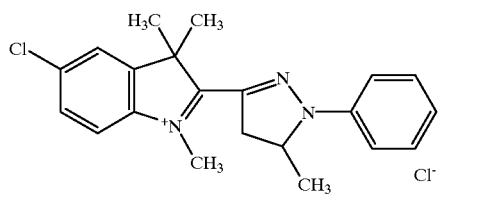

-continued

Compound (o)
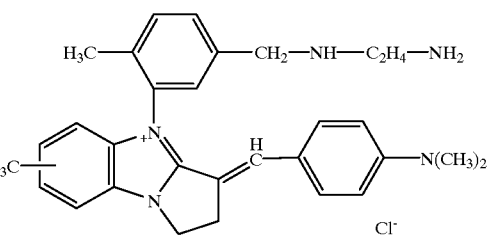

Compound (p)
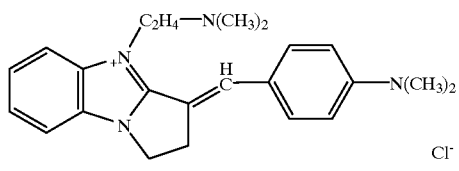

Compound (q)
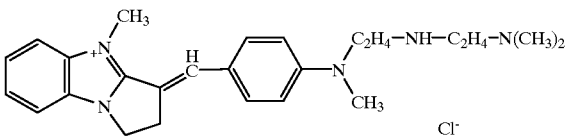

At least one of these direct dyes (1) can be used or they may be used in combination with another direct dye. In particular, when the direct dye (1) is a yellow dye, combination with red and blue dyes makes it possible to dye the hair with a deep and highly lustrous dark brown or black color.

Examples of the direct dye other than the direct dyes (1) include Basic Blue 7 (C. I. 42595), Basic Blue 26 (C. I. 44045), Basic Blue 99 (C. I. 56059), Basic Violet 10 (C. I. 45170), Basic Violet 14 (C. I. 42515), Basic Brown 16 (C. I. 12250), Basic Brown 17 (C. I. 12251), Basic Red 2 (C. I. 50240), Basic Red 22 (C. I. 11055), Basic Red 76 (C. I. 12245), Basic Red 118 (C. I. 12251:1) and Basic Yellow 57 (C. I. 12719); and basic dyes as described in Japanese Patent Publication No. Sho 58-2204, Japanese Patent Application Laid-Open (kokai) No. Hei 9-118832, Japanese Language Laid-Open Publication (PCT) No. Hei 8-501322 or Japanese Language Laid-Open Publication (PCT) No. Hei 8-507545.

The direct dye (1) is preferably added in an amount of 0.01 to 20 wt. %, more preferably 0.05 to 10 wt. %, especially 0.1 to 5 wt. % based on the whole composition (after mixture of all the component parts when the composition is a two part or three part composition; this will apply equally hereinafter). When another direct dye is added in combination, the content of it in total with the direct dye (1) preferably ranges from 0.05 to 10 wt. %, especially 0.1 to 5 wt. %.

The hair dye composition of the present invention is preferably adjusted to pH 6 to 11, with pH 8 to 11 being especially preferred. Examples of the alkali agent to be used for pH adjustment include ordinarily employed ones such as ammonia, organic amines and salts thereof. The alkali agent is preferably added in an amount of 0.01 to 20 wt. %, more preferably 0.1 to 10 wt. %, especially 0.5 to 5 wt. % based on the whole composition.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate, perborates such as sodium perborate, percarbonates such as sodium percarbonate and bromates such as sodium bromate and potassium bromate are usable. Out of them, hydrogen peroxide is especially preferred. The oxidizing agent is added in an amount of 0.5 to 10 wt. %, especially 1 to 8 wt. %, based on the whole composition.

In the hair dye composition of the present invention, an oxidation dye can be incorporated further. This incorporation enables markedly vivid dyeing not attainable by the single use of an oxidation dye. The above-exemplified oxidizing agents can be used as an oxidizing agent, with hydrogen peroxide being particularly preferred. Alternatively, an oxidizing enzyme such as laccase can be employed. For the oxidation dye, known color developers and couplers ordinarily employed for an oxidation type hair dye can be used.

Examples of the developer include p-phenylenediamines having one or several groups selected from $NH_2$—, NHR— and $NR_2$-groups (in which R represents a $C_{1-4}$ alkyl or hydroxyalkyl group) such as p-phenylenediamine, p-toluylenediamine, N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-p-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives and 4,5-diaminopyrazole derivatives; p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropyl-bis(N-hydroxyethyl-p-phenylenediamine); and salts thereof.

Examples of the coupler include 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluylenediamine, resorcin, m-phenylenediamine, m-aminophenol, 4-chlororesorcin, 2-methylresorcin, 2,4-diaminophenoxyethanol, 2,6-diaminopyridine, 2-amino-3-hydroxypyridine, 4-hydroxyindole, 6-hydroxyindole, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine and 1,3-bis(2,4-diaminophenoxy)propane; and salts thereof.

At least one of the above-exemplified ones as each of the developer and coupler can be used. The content of each of the developer and coupler is preferably 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

When an anionic component (such as anionic surfactant or anionic polymer) is added to the hair dye composition of the present invention, it is preferred to satisfy the following equation:

"Ion activity concentration of the anionic component/ion activity concentration of the cationic direct dye (1)≦8"

The term "ion activity concentration" as used herein means "molar concentration×ionic valence".

Addition of a polyol, polyol alkyl ether, cationic or amphoteric polymer or silicone to the hair dye composition of the present invention is preferred, because the resulting composition can dye the hair uniformly and has improved cosmetic effects of the hair.

In addition to the above-described components, those ordinarily employed as a raw material for cosmetics can be added to the hair dye composition of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first component part containing an alkali agent and a second component part containing an oxidizing agent, or a three-part composition having, in addition to these two component parts, a powdery oxidizing agent such as persulfate. The direct dye (1) can be incorporated in either one or both of these component parts of the two-part or three-part composition. When the hair dye composition of the present invention is one-part type, it is applied to the hair directly, while the two- or three-part type is applied to the hair after mixing these parts upon hair dyeing.

No particular limitation is imposed on the form of the hair dye composition of the present invention. Examples include powder, transparent liquid, emulsion, cream, gel, paste, aerosol, and aerosol foam. It preferably has a viscosity of 2000 to 100000 mPa·s in the stage of application to the hair (after mixing of all the component parts when the composition is a two-part or three-part type).

EXAMPLES

Examples 1 to 5

In a manner known per se in the art, hair dyes as shown in Table 1 were prepared.

TABLE 1

| (wt. %) | Examples | | | | |
| --- | --- | --- | --- | --- | --- |
|  | 1 | 2 | 3 | 4 | 5 |
| Dye [Compound (a)] | 0.2 |  | 0.15 | 0.1 |  |
| Dye [Compound (c)] |  | 0.5 |  | 0.1 | 0.2 |
| Dye [formula (I), Red] |  |  | 0.15 | 0.1 | 0.05 |
| Dye [formula (II), Yellow] |  |  | 0.1 | 0.1 |  |
| Ethanol |  | 5 |  | 5 | 5 |
| Propylene glycol |  |  | 5 |  | 5 |
| Diethylene glycol monomethyl ether |  | 10 |  |  |  |
| Guar gum | 1 |  |  |  |  |
| Hydroxypropyl guar gum |  | 1 | 1 | 1 | 1 |

TABLE 1-continued

| (wt. %) | Examples | | | | |
|---|---|---|---|---|---|
| | 1 | 2 | 3 | 4 | 5 |
| "Gufquat 734" (trade name; product of ISP Japan) | 1 | | 1 | | |
| "Catinal LC100" (trade name; product of Toho Chemical Industry) | | 1 | | | 1 |
| "Polyether-modified silicone KF6005" (trade name; product of Shin-Etsu Chemical) | | | | 0.4 | |
| "Amodimethicone SM8702C" (trade name; product of Dow Corning Toray Silicone) | | | | | 1.5 |
| Monoethanolamine | 0.1 | | | | |
| Phosphoric acid | Amount to adjust pH to 9 | | | | |
| Perfume | q.s. | | | | |
| Water | Balance | | | | |

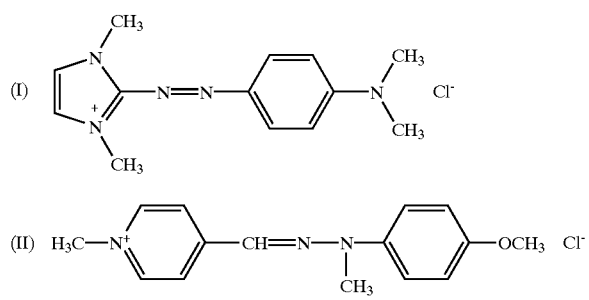

(I), (II) chemical structures

Examples 6 to 9

In a manner known per se in the art, hair dyes as shown in Table 2 were prepared.

TABLE 2

| (wt. %) | Examples | | | |
|---|---|---|---|---|
| | 6 | 7 | 8 | 9 |
| 1st part | | | | |
| Dye [Compound (a)] | 0.2 | | 0.15 | 0.2 |
| Dye [Compound (b)] | | 0.1 | 0.15 | |
| Dye [formula (I), Red] | | 0.1 | | 0.05 |
| Dye [Basic Blue 99] | | 0.3 | | |
| 28 wt. % Aqueous ammonia | 5 | | | |
| Monoethanolamine | 2 | | | |
| Propylene glycol | 8 | | | |
| Polyoxyethylene (20) isostearyl ether | 24 | | | |
| Polyoxyethylene (2) isostearyl ether | 20 | | | |
| "Merquat 280" (trade name; product of Calgon Corp., a 35 wt. % aqueous solution) | 8 | | | |
| "Polymer JR400" (trade name; product of Union Carbide) | | 0.5 | | 0.5 |
| "Amodimethicone SM8702C" (trade name; product of Dow Corning Toray Silicone) | | 2 | | |
| "Polyether modified silicone KF6005" (trade name; product of Shin-Etsu Chemical) | | | | 0.3 |
| Tetrasodium ethylenediaminetetraacetate | 0.1 | | | |
| Perfume | q.s. | | | |
| Ammonium chloride | Amount to adjust pH to 10 | | | |
| Water | Balance | | | |
| 2nd part | | | | |
| 35 wt. % Aqueous hydrogen peroxide | 17.1 | | | |
| Methylparaben | 0.1 | | | |
| Phosphoric acid | Amount to adjust pH to 3.5 | | | |
| Water | Balance | | | |

Examples 10 to 12

In a manner known per se in the art, hair dyes as shown in Table 3 were prepared.

TABLE 3

| (wt. %) | Examples | | |
|---|---|---|---|
| | 10 | 11 | 12 |
| 1st part | | | |
| Toluene-2,5-diamine | 1.9 | 1 | |
| Para-aminophenol | | | 1 |
| Resorcin | 2 | | |
| Para-amino-ortho-cresol | | | 1.1 |
| 2,4-Diaminophenoxyethanol | | 1.37 | |
| Dye [Compound (a)] | 0.05 | | |
| Dye [Compound (m)] | | 0.15 | |
| Dye [Compound (k)] | | | 0.1 |
| 28 wt. % Aqueous ammonia | 5 | | |
| Monoethanolamine | 2 | | |
| Propylene glycol | 8 | | |
| Polyoxyethylene (20) isostearyl ether | 24 | | |
| Polyoxyethylene (2) isostearyl ether | 20 | | |
| "Merquat 280" (trade name; product of Calgon Corp., a 35 wt. % aqueous solution) | 8 | | |
| "Polymer JR400" (trade name; product of Union Carbide) | | 0.5 | |
| "Amodimethicone SM8702C" (trade name; product of Dow Corning Toray Silicone) | | | 2 |
| Sodium sulfite | 0.05 | | |
| Ascorbic acid | 0.5 | | |
| Tetrasodium ethylenediaminetetraacetate | 0.1 | | |
| Perfume | q.s. | | |
| Ammonium chloride | Amount to adjust pH to 10 | | |
| Water | Balance | | |
| 2nd part | | | |
| 35 wt. % Aqueous hydrogen peroxide | 17.1 | | |
| Methylparaben | 0.1 | | |
| Phosphoric acid | Amount to adjust pH to 3.5 | | |
| Water | Balance | | |

Example 13

In a manner known per se in the art, the following hair dye was prepared.

| | (wt. %) |
|---|---|
| (First part) | |
| Para-aminophenol | 1 |
| Para-amino-ortho-cresol | 1.1 |
| Compound (q) | 0.1 |
| 28 wt. % Aqueous ammonia | 5 |
| Monoethanolamine | 2 |
| Cetanol | 8.5 |
| Polyoxyethylene (40) cetyl ether | 3 |
| Polyoxyethylene (2) cetyl ether | 3.5 |
| Stearyl trimethyl ammonium chloride | 2 |
| Liquid paraffin | 0.5 |
| Sodium sulfite | 0.05 |
| Ascorbic acid | 0.5 |
| Tetrasodium ethylenediaminetetraacetate | 0.1 |
| Perfume | q.s. |
| Ammonium chloride | Amount to adjust pH to 10 |
| Water | Balance |

-continued

| | (wt. %) |
|---|---|
| (Second part) | |
| 35 wt. % Aqueous hydrogen peroxide | 17.1 |
| Methylparaben | 0.1 |
| Phosphoric acid | Amount to adjust pH to 3.5 |
| Water | Balance |

What is claimed is:

1. A hair dye composition, comprising:
a one-part aqueous formulation containing a direct dye compound represented by formula (1):

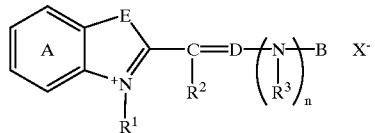

(1)

wherein, ring A represents a benzene ring which may have a substituent and may be cyclocondensed with another aromatic ring;

B represents an aryl group which may have a substituent or may be coupled with $R^2$ to form a heterocyclic structure, or a heterocyclic group which may have a substituent or may be coupled with $R^2$ to form a heterocyclic structure, D represents a nitrogen atom or a group $CR^4$, wherein $R^4$ represents a hydrogen atom or a $C_{1-6}$ alkyl group;

E represents a group $NR^5$, $CR^6R^7$ or $CR^6\!=\!CR^7$, wherein $R^5$ represents a $C_{1-6}$ alkyl group which may have a substituent, a $C_{2-6}$ alkenyl group which may have a substituent or an aryl group which may have a substituent, or forms, when taken together with $R^2$, a ring, and $R^6$ and $R^7$ each independently represents a hydrogen atom or a $C_{1-6}$ alkyl group, an oxygen atom or a sulfur atom;

$R^1$ represents a $C_{1-6}$ alkyl group which may have a substituent, a $C_{2-6}$ alkenyl group which may have a substituent or an aryl group which may have a substituent;

$R^2$ represents a divalent group bonded to B or forms a ring, when taken together with $R^3$ or $R^5$, $R^3$ forms a ring when taken together with $R^2$;

n is 0 or 1, with the proviso that when n=0, $R^2$ and $R^5$, when taken together with N—C—C, form a 5- to 7-membered nitrogen-containing heterocyclic structure which may have a substituent, or $R^2$ is bonded to B, thereby forming a 6- or 7-membered heterocyclic structure which may have a substituent and may contain a hetero atom other than D and when n=1, $R^2$ and $R^3$, when taken together with C=D—N, form a 5- to 7-membered nitrogen-containing heterocyclic structure which may have a substituent; and $X^-$ represents an anion, the composition having a pH ranging from 6–11 that is adjusted to within said range by an alkali agent and containing at least one cosmetic ingredient selected from the group consisting of hydrocarbons, animal or vegetable fats and oils, fatty acids, organic solvents, hair penetration promoters, cationic surfactants, natural or synthetic polymers, alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes, aerosolizing agents and UV absorbers.

2. A hair dye composition, comprising:
a two-part aqueous formulation comprising, in a first part, a direct dye compound represented by formula (1):

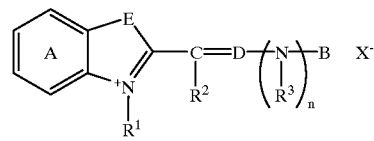

(1)

wherein, ring A represents a benzene ring which may have a substituent and may be cyclocondensed with another aromatic ring;

B represents an aryl group which may have a substituent or may be coupled with $R^2$ to form a heterocyclic structure, or a heterocyclic group which may have a substituent or may be coupled with $R^2$ to form a heterocyclic structure, D represents a nitrogen atom or a group $CR^4$, wherein $R^4$ represents a hydrogen atom or a $C_{1-6}$ alkyl group;

E represents a group $NR^5$, $CR^6R^7$ or $CR^6\!=\!CR^7$, wherein $R^5$ represents a $C_{1-6}$ alkyl group which may have a substituent, a $C_{2-6}$ alkenyl group which may have a substituent or an aryl group which may have a substituent, or forms, when taken together with $R^2$, a ring, and $R^6$ and $R^7$ each independently represents a hydrogen atom or a $C_{1-6}$ alkyl group, an oxygen atom or a sulfur atom;

$R^1$ represents a $C_{1-6}$ alkyl group which may have a substituent, a $C_{2-6}$ alkenyl group which may have a substituent or an aryl group which may have a substituent;

$R^2$ represents a divalent group bonded to B or forms a ring, when taken together with $R^3$ or $R^5$, $R^3$ forms a ring when taken together with $R^2$;

n is 0 or 1, with the proviso that when n=0, $R^2$ and $R^5$, when taken together with N—C—C, form a 5- to 7-membered nitrogen-containing heterocyclic structure which may have a substituent, or $R^2$ is bonded to B, thereby forming a 6- or 7-membered heterocyclic structure which may have a substituent and may contain a hetero atom other than D and when n=1, $R^2$ and $R^3$, when taken together with C=D—N, form a 5- to 7-membered nitrogen-containing heterocyclic structure which may have a substituent; and $X^-$ represents an anion; the first part having a pH ranging from 6–11 that is adjusted to within said range by an alkali agent; and a second part, comprising an aqueous solution of an oxidizing agent.

3. A hair dye composition, comprising:
a three-part aqueous formulation comprising, in a first part, a direct dye compound represented by formula (1):

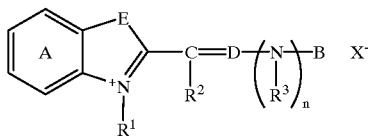

wherein, ring A represents a benzene ring which may have a substituent and may be cyclocondensed with another aromatic ring;

B represents an aryl group which may have a substituent or may be coupled with $R^2$ to form a heterocyclic structure, or a heterocyclic group which may have a substituent or may be coupled with $R^2$ to form a heterocyclic structure, D represents a nitrogen atom or a group $CR^4$, wherein $R^4$ represents a hydrogen atom or a $C_{1-6}$ alkyl group;

E represents a group $NR^5$, $CR^6R^7$ or $CR^6=CR^7$, wherein $R^5$ represents a $C_{1-6}$ alkyl group which may have a substituent, a $C_{2-6}$ alkenyl group which may have a substituent or an aryl group which may have a substituent, or forms, when taken together with $R^2$, a ring, and $R^6$ and $R^7$ each independently represents a hydrogen atom or a $C_{1-6}$ alkyl group, an oxygen atom or a sulfur atom;

$R^1$ represents a $C_{1-6}$ alkyl group which may have a substituent, a $C_{2-6}$ alkenyl group which may have a substituent or an aryl group which may have a substituent;

$R^2$ represents a divalent group bonded to B or forms a ring, when taken together with $R^3$ or $R^5$, $R^3$ forms a ring when taken together with $R^2$;

n is 0 or 1, with the proviso that when n=0, $R^2$ and $R^5$, when taken together with N—C—C, form a 5- to 7-membered nitrogen-containing heterocyclic structure which may have a substituent, or $R^2$ is bonded to B, thereby forming a 6- or 7-membered heterocyclic structure which may have a substituent and may contain a hetero atom other than D and when n=1, $R^2$ and $R^3$, when taken together with C=D—N, form a 5- to 7-membered nitrogen-containing heterocyclic structure which may have a substituent; and $X^-$ represents an anion; the first part having a pH ranging from 6–11 that is adjusted to within said range by an alkali agent;

a second part, comprising an aqueous solution of an oxidizing agent; and a third part, comprising a powdered oxidizing agent.

4. The hair dye composition according to claim 1, wherein the content of alkali in the composition ranges from 0.01 to 20 wt % of the formulation.

5. The hair dye composition according to claim 2, wherein the oxidizing agent is hydrogen peroxide, a persulfate, a perborate, a percarbonate or a bromate.

6. The hair dye composition according to claim 2, wherein the oxidizing agent is present in the entire composition in an amount of 0.5 to 10 wt %.

7. The hair dye composition according to claim 2, wherein the oxidizing agent is combined with a developer and a coupler in the second part of the composition, each present in an amount ranging from 0.01 to 20 wt % of the entire composition.

8. The hair dye composition according to claim 3, wherein the oxidizing agent of the second part is hydrogen peroxide, a persulfate, a perborate, a percarbonate or a bromate.

9. The hair dye composition according to claim 3, wherein the oxidizing agent of the second part is present in the entire composition in an amount of 0.5 to 10 wt %.

10. The hair dye composition according to claim 3, wherein the oxidizing agent is combined with a developer and a coupler in the second part of the composition, each present in an amount ranging from 0.01 to 20 wt % of the entire composition.

11. The hair dye composition according to claim 3, wherein the third part of the composition contains a powdered persulfate oxidizing agent.

12. A method of dyeing hair, comprising:

treating the hair with a one-part aqueous formulation containing a direct dye compound represented by formula (1):

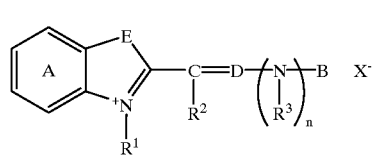

wherein, ring A represents a benzene ring which may have a substituent and may be cyclocondensed with another aromatic ring;

B represents an aryl group which may have a substituent or may be coupled with $R^2$ to form a heterocyclic structure, or a heterocyclic group which may have a substituent or may be coupled with $R^2$ to form a heterocyclic structure, D represents a nitrogen atom or a group $CR^4$, wherein $R^4$ represents a hydrogen atom or a $C_{1-6}$ alkyl group;

E represents a group $NR^5$, $CR^6R^7$ or $CR^6=CR^7$, wherein $R^5$ represents a $C_{1-6}$ alkyl group which may have a substituent, a $C_{2-6}$ alkenyl group which may have a substituent or an aryl group which may have a substituent, or forms, when taken together with $R^2$, a ring, and $R^6$ and $R^7$ each independently represents a hydrogen atom or a $C_{1-6}$ alkyl group, an oxygen atom or a sulfur atom;

$R^1$ represents a $C_{1-6}$ alkyl group which may have a substituent, a $C_{2-6}$ alkenyl group which may have a substituent or an aryl group which may have a substituent;

$R^2$ represents a divalent group bonded to B or forms a ring, when taken together with $R^3$ or $R^5$, $R^3$ forms a ring when taken together with $R^2$;

n is 0 or 1, with the proviso that when n=0, $R^2$ and $R^5$, when taken together with N—C—C, form a 5- to 7-membered nitrogen-containing heterocyclic structure which may have a substituent, or $R^2$ is bonded to B, thereby forming a 6- or 7-membered heterocyclic structure which may have a substituent and may contain a hetero atom other than D and when n=1, $R^2$ and $R^3$, when taken together with C=D—N, form a 5- to 7-membered nitrogen-containing heterocyclic structure which may have a substituent; and $X^-$ represents an anion; the composition having a pH ranging from 6–11 that is adjusted to within said range by an alkali agent and containing at least one cosmetic ingredient selected from the group consisting of hydrocarbons, animal or vegetable fats and oils, fatty acids, organic solvents, hair penetration promoters, cationic surfactants, natural or synthetic polymers, alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes, aerosolizing agents and UV absorbers.

13. A method of dyeing hair, comprising:

treating the hair with a two-part aqueous formulation comprising, in a first part, a direct dye compound represented by formula (1):

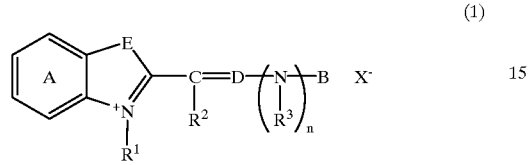

(1)

wherein, ring A represents a benzene ring which may have a substituent and may be cyclocondensed with another aromatic ring;

B represents an aryl group which may have a substituent or may be coupled with $R^2$ to form a heterocyclic structure, or a heterocyclic group which may have a substituent or may be coupled with $R^2$ to form a heterocyclic structure, D represents a nitrogen atom or a group $CR^4$, wherein $R^4$ represents a hydrogen atom or a $C_{1-6}$ alkyl group;

E represents a group $NR^5$, $CR^6R^7$ or $CR^6 = CR^7$, wherein $R^5$ represents a $C_{1-6}$ alkyl group which may have a substituent, a $C_{2-6}$ alkenyl group which may have a substituent or an aryl group which may have a substituent, or forms, when taken together with $R^2$, a ring, and $R^6$ and $R^7$ each independently represents a hydrogen atom or a $C_{1-6}$ alkyl group, an oxygen atom or a sulfur atom;

$R^1$ represents a $C_{1-6}$ alkyl group which may have a substituent, a $C_{2-6}$ alkenyl group which may have a substituent or an aryl group which may have a substituent;

$R^2$ represents a divalent group bonded to B or forms a ring, when taken together with $R^3$ or $R^5$, $R^3$ forms a ring when taken together with $R^2$;

n is 0 or 1, with the proviso that when n=0, $R^2$ and $R^5$, when taken together with N—C—C, form a 5- to 7-membered nitrogen-containing heterocyclic structure which may have a substituent, or $R^2$ is bonded to B, thereby forming a 6- or 7-membered heterocyclic structure which may have a substituent and may contain a hetero atom other than D and when n=1, $R^2$ and $R^3$, when taken together with C=D—N, form a 5- to 7-membered nitrogen-containing heterocyclic structure which may have a substituent; and $X^-$ represents an anion; the first part having a pH ranging from 6–11 that is adjusted to within said range by an alkali agent; and a second part, comprising an aqueous solution of an oxidizing agent.

14. A method of dyeing hair, comprising:

treating the hair with a three-part aqueous formulation comprising, in a first part, a direct dye compound represented by formula (1):

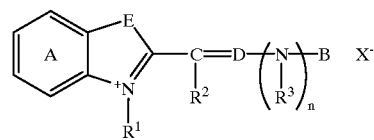

(1)

wherein, ring A represents a benzene ring which may have a substituent and may be cyclocondensed with another aromatic ring;

B represents an aryl group which may have a substituent or may be coupled with $R^2$ to form a heterocyclic structure, or a heterocyclic group which may have a substituent or may be coupled with $R^2$ to form a heterocyclic structure, D represents a nitrogen atom or a group $CR^4$, wherein $R^4$ represents a hydrogen atom or a $C_{1-6}$ alkyl group;

E represents a group $NR^5$, $CR^6R^7$ or $CR^6 = CR^7$, wherein $R^5$ represents a $C_{1-6}$ alkyl group which may have a substituent, a $C_{2-6}$ alkenyl group which may have a substituent or an aryl group which may have a substituent, or forms, when taken together with $R^2$, a ring, and $R^6$ and $R^7$ each independently represents a hydrogen atom or a $C_{1-6}$ alkyl group, an oxygen atom or a sulfur atom;

$R^1$ represents a $C_{1-6}$ alkyl group which may have a substituent, a $C_{2-6}$ alkenyl group which may have a substituent or an aryl group which may have a substituent;

$R^2$ represents a divalent group bonded to B or forms a ring, when taken together with $R^3$ or $R^5$, $R^3$ forms a ring when taken together with $R^2$;

n is 0 or 1, with the proviso that when n=0, $R^2$ and $R^5$, when taken together with N—C—C, form a 5- to 7-membered nitrogen-containing heterocyclic structure which may have a substituent, or $R^2$ is bonded to B, thereby forming a 6- or 7-membered heterocyclic structure which may have a substituent and may contain a hetero atom other than D and when n=1, $R^2$ and $R^3$, when taken together with C=D—N, form a 5- to 7-membered nitrogen-containing heterocyclic structure which may have a substituent; and $X^-$ represents an anion; the first part having a pH ranging from 6–11 that is adjusted to within said range by an alkali agent;

a second part, comprising an aqueous solution of an oxidizing agent; and a third part, comprising a powdered oxidizing agent.

15. A hair dye composition, comprising:

a one-part aqueous formulation containing a direct dye compound represented by formula (1):

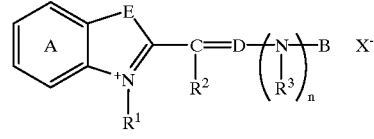

(1)

wherein, ring A represents a benzene ring which may have a substituent and may be cyclocondensed with another aromatic ring;

B represents an aryl group which may have a substituent or may be coupled with $R^2$ to form a heterocyclic structure, or a heterocyclic group which may have a substituent or may be coupled with $R^2$ to form a heterocyclic structure, D represents a nitrogen atom or a group $CR^4$, wherein $R^4$ represents a hydrogen atom or a $C_{1-6}$ alkyl group;

E represents a group $NR^5$, $CR^6R^7$ or $CR^6{=}CR^7$, wherein $R^5$ represents a $C_{1-6}$ alkyl group which may have a substituent, a $C_{2-6}$ alkenyl group which may have a substituent or an aryl group which may have a substituent, or forms, when taken together with $R^2$, a ring, and $R^6$ and $R^7$ each independently represents a hydrogen atom or a $C_{1-6}$ alkyl group, an oxygen atom or a sulfur atom;

$R^1$ represents a $C_{1-6}$ alkyl group which may have a substituent, a $C_{2-6}$ alkenyl group which may have a substituent or an aryl group which may have a substituent;

$R^2$ represents a divalent group bonded to B or forms a ring, when taken together with $R^3$ or $R^5$, $R^3$ forms a ring when taken together with $R^2$;

n is 0 or 1, with the proviso that when n=0, $R^2$ and $R^5$, when taken together with N—C—C, form a 5- to 7-membered nitrogen-containing heterocyclic structure which may have a substituent, or $R^2$ is bonded to B, thereby forming a 6- or 7-membered heterocyclic structure which may have a substituent and may contain a hetero atom other than D and when n=1, $R^2$ and $R^3$, when taken together with C=D—N, form a 5- to 7-membered nitrogen-containing heterocyclic structure which may have a substituent and with the proviso that the group in formula (1) of —$CR^2{=}D{-}(NR^3)_n$—B can not be an amino substituted quinoline group; and $X^-$ represents an anion, the composition having a pH ranging from 6–11 that is adjusted to within said range by an alkali agent and containing at least one cosmetic ingredient selected from the group consisting of hydrocarbons, animal or vegetable fats and oils, fatty acids, organic solvents, hair penetration promoters, cationic surfactants, natural or synthetic polymers, alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes, aerosolizing agents and UV absorbers.

16. A hair dye composition, comprising:

a two-part aqueous formulation comprising, in a first part, a direct dye compound represented by formula (1):

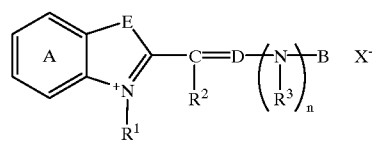

(1)

wherein, ring A represents a benzene ring which may have a substituent and may be cyclocondensed with another aromatic ring;

B represents an aryl group which may have a substituent or may be coupled with $R^2$ to form a heterocyclic structure, or a heterocyclic group which may have a substituent or may be coupled with $R^2$ to form a heterocyclic structure, D represents a nitrogen atom or a group $CR^4$, wherein $R^4$ represents a hydrogen atom or a $C_{1-6}$ alkyl group;

E represents a group $NR^5$, $CR^6R^7$ or $CR^6{=}CR^7$, wherein $R^5$ represents a $C_{1-6}$ alkyl group which may have a substituent, a $C_{2-6}$ alkenyl group which may have a substituent or an aryl group which may have a substituent, or forms, when taken together with $R^2$, a ring, and $R^6$ and $R^7$ each independently represents a hydrogen atom or a $C_{1-6}$ alkyl group, an oxygen atom or a sulfur atom;

$R^1$ represents a $C_{1-6}$ alkyl group which may have a substituent, a $C_{2-6}$ alkenyl group which may have a substituent or an aryl group which may have a substituent;

$R^2$ represents a divalent group bonded to B or forms a ring, when taken together with $R^3$ or $R^5$, $R^3$ forms a ring when taken together with $R^2$;

n is 0 or 1, with the proviso that when n=0, $R^2$ and $R^5$, when taken together with N—C—C, form a 5- to 7-membered nitrogen-containing heterocyclic structure which may have a substituent, or $R^2$ is bonded to B, thereby forming a 6- or 7-membered heterocyclic structure which may have a substituent and may contain a hetero atom other than D and when n=1, $R^2$ and $R^3$, when taken together with C=D—N, form a 5- to 7-membered nitrogen-containing heterocyclic structure which may have a substituent and with the proviso that the group in formula (1) of —$CR^2{=}D{-}(NR^3)_n$—B can not be an amino substituted quinoline group; and $X^-$ represents an anion; the first part having a pH ranging from 6–11 that is adjusted to within said range by an alkali agent; and a second part, comprising an aqueous solution of an oxidizing agent.

17. A hair dye composition, comprising:

a three-part aqueous formulation comprising, in a first part, a direct dye compound represented by formula (1):

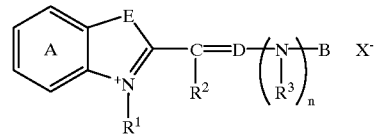

(1)

wherein, ring A represents a benzene ring which may have a substituent and may be cyclocondensed with another aromatic ring;

B represents an aryl group which may have a substituent or may be coupled with $R^2$ to form a heterocyclic structure, or a heterocyclic group which may have a substituent or may be coupled with $R^2$ to form a heterocyclic structure, D represents a nitrogen atom or a group $CR^4$, wherein $R^4$ represents a hydrogen atom or a $C_{1-6}$ alkyl group;

E represents a group $NR^5$, $CR^6R^7$ or $CR^6{=}CR^7$, wherein $R^5$ represents a $C_{1-6}$ alkyl group which may have a substituent, a $C_{2-6}$ alkenyl group which may have a substituent or an aryl group which may have a substituent, or forms, when taken together with $R^2$, a ring, and $R^6$ and $R^7$ each independently represents a hydrogen atom or a $C_{1-6}$ alkyl group, an oxygen atom or a sulfur atom;

$R^1$ represents a $C_{1-6}$ alkyl group which may have a substituent, a $C_{2-6}$ alkenyl group which may have a substituent or an aryl group which may have a substituent;

R² represents a divalent group bonded to B or forms a ring, when taken together with R³ or R⁵, R³ forms a ring when taken together with R²;

n is 0 or 1, with the proviso that when n=0, R² and R⁵, when taken together with N—C—C, form a 5- to 7-membered nitrogen-containing heterocyclic structure which may have a substituent, or R² is bonded to B, thereby forming a 6- or 7-membered heterocyclic structure which may have a substituent and may contain a hetero atom other than D and when n=1, R² and R³, when taken together with C=D—N, form a 5- to 7-membered nitrogen-containing heterocyclic structure which may have a substituent and with the proviso that the group in formula (1) of —CR²=D—(NR³)$_n$—B can not be an amino substituted quinoline group; and X⁻ represents an anion; the first part having a pH ranging from 6–11 that is adjusted to within said range by an alkali agent;

a second part, comprising an aqueous solution of an oxidizing agent; and a third part, comprising a powdered oxidizing agent.

* * * * *